US006797464B2

(12) United States Patent
Stevenson et al.

(10) Patent No.: US 6,797,464 B2
(45) Date of Patent: Sep. 28, 2004

(54) DETECTION OF DRUG-RESISTANT HUMAN IMMUNODEFICIENCY VIRUS

(75) Inventors: Mario Stevenson, Shrewsbury, MA (US); Mark Sharkey, Oxford, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 10/192,369

(22) Filed: Jul. 10, 2002

(65) Prior Publication Data

US 2004/0009124 A1 Jan. 15, 2004

(51) Int. Cl.[7] .............................. C12Q 1/70; C12Q 1/68; C12P 19/34; C07H 21/02
(52) U.S. Cl. .............................. 435/5; 435/6; 435/91.2; 536/23.1
(58) Field of Search .............................. 435/5, 6, 91.2; 536/23.1

(56) References Cited

U.S. PATENT DOCUMENTS

| | | | |
|---|---|---|---|
| 5,703,086 A | 12/1997 | Bukrinsky et al. | 514/275 |
| 5,753,674 A | 5/1998 | Kun et al. | 514/309 |
| 5,872,210 A | 2/1999 | Medabalimi | 530/327 |
| 6,331,389 B1 | 12/2001 | Lieven et al. | 435/536 |

OTHER PUBLICATIONS

Gunthard et al, "Human immunodeficiency virus replication and genotypic resistance in blood and lymph nodes after a year of potent antiretroviral therapy", J. Virol. (1998) 72(3):2422–2428.*
Uberla et al "Animal model for the therapy of acquired immunodeficiency syndrome with reverse transcriptase inhibitors", Proc. Natl. Acad. Sci. (1995) 92:8210–8214.*
Chun et al., "Presence of an inducible HIV–1 latent reservoir during highly active antiretroviral therapy", Proc. Natl. Acad. Sci. 94:13193–97 (Nov. 1997).
Günthard et al., "Human Immunodeficiency virus replication and genotypic resistance in blood and lymph nodes after a year of potent antiretroviral therapy", J. Virol. 72(3):2422–2428 (Mar. 1998).
Wang et al., "Molecular evidence for drug–induced compartmentalization of HIV–1 quasispecies in a patient with periodic changes to HAART", AIDS 14(15): 2265–2272 (2000).
Zazzi et al., "Evaluation of the presence of 2–LTR HIV–1 unintegrated DNA as a simple molecular predictor of disease progression", J. Med. Virol. 52:20–25 (1997).
Brown et al. "Correct Integration of Retroviral DNA In Vitro" Cell 49:347–356 (1987).
Bukrinsky et al. "Active nuclear import of human immunodeficiency virus type 1 preintegration complexes" Proc. Natl. Acad. Sci. USA 89:6580–6584 (1992).
Clayman et al. "Circular Forms of DNA Synthesized by Rous Sarcoma Virus in vitro" Science 206: 582–584 (1979).
D'Aquila et al. "Drug Resistance Mutations HIV–1" International AIDS Society—USA 10(2):11–15 (2002).
Jurriaans et al. "Analysis of human immunodeficiency virus type 1 LTR–LTR junctions in peripheral blood mononuclear cells of infected individuals" Journal of General Virology 73:1537–1541 (1992).
Panther et al. "Unintegrated Circular HIV–1 DNA in the Peripheral Mononuclear Cells of HIV–1–Infected Subjects: Association With High Levels of Plasma IIIV–1 RNA, Rapid Decline in CD4 Count, and Clinical Progression to Aids" Journal of Acquired Immune Deficiency Syndromes and Human Retrovirology 17:303–313 (1998).
Pauza et al., "2–LTR Circular Viral DNA as a Marker for Human Immunodeficiency Virus Type 1 Infection in Vivo" Virology 205:470–478 (1994).
Piatek et al., "Molecular beacon sequence analysis for detecting drug resistance in Mycobacterium tuberculosis" Nature Biotechnology 16:359–363 (1998).
Shafer "Interlaboratory Variability in HIV Drug Resistance Testing" HIVresistanceWeb (2001).
Shank et al. "Virus–Specific DNA in the Cytoplasm of Avian Sarcoma Virus–Infected Cells Is a Precursor to Convalently Closed Circular Viral DNA in the Nucleus" J. Virol. 25:104–114 (1978).
Stevenson et al., "HIV–1 replication is controlled at the level of 1 cell activation and proviral integration" The EMBO Journal 9(5):1551–1560 (1990).
Stevenson et al., "Integration Is Not Necessary for Expression of Human Immunodeficiency Virus Type 1 Protein Products" Journal of Virology 64:2421–2425 (1990).

* cited by examiner

Primary Examiner—Jeffrey Fredman
(74) Attorney, Agent, or Firm—Fish & Richardson P.C.

(57) ABSTRACT

The invention relates to methods of detecting a drug resistant HIV in a subject. The methods include detecting mutations associated with drug resistance in an HIV 2-LTR circle DNA molecule obtained from a cell of an HIV-positive subject, e.g, an HIV-1-positive human.

24 Claims, 5 Drawing Sheets

DETECTION OF DRUG-RESISTANT HUMAN IMMUNODEFICIENCY VIRUS

STATEMENT AS TO FEDERALLY-SPONSORED RESEARCH

The invention was made with Government grants from the National Institutes of Health (RR11589, HL57880, AI32391, and AI32907). The Government has certain rights in the invention.

FIELD OF THE INVENTION

The invention relates to human immunodeficiency virus (HIV) detection assays, particularly to detection of drug-resistant HIV.

BACKGROUND OF THE INVENTION

Various assays have been developed to detect HIV. A common HIV-1 detection assay utilizes quantitative polymerase chain reaction (PCR) as a means to amplify and detect viral RNA present in patient plasma. HIV-1 positive individuals undergoing combination antiviral therapy (i.e., receiving two or more anti-HIV-1 compounds) can exhibit decreased viral loads in the peripheral blood. In some cases, after several weeks or months of therapy, HIV-1 RNA cannot be detected in the peripheral blood, indicating possible eradication of HIV-1 in those individuals. Unfortunately, if patients exhibiting such a seemingly negative result stop therapy in the face of continued viral replication below the sensitivity of detection assays, the HIV can rebound very rapidly. Thus, the limited sensitivity of HIV detection assays provides a challenge to further advances in therapy.

Highly active antiretroviral therapy (HAART) with reverse transcriptase and protease inhibitors markedly suppresses HIV replication in the majority of infected patients. However, in a significant percentage of patients, viruses acquire mutations in their reverse transcriptase and protease genes that confer decreased sensitivity to the reverse transcriptase and protease inhibitors. This leads to drug failure, a resumption of viral replication, and a negative impact on patient survival. To combat drug resistance, clinicians switch therapies to drug combinations not previously administered to the patient. However, drug resistance mutations can confer resistance to a broad spectrum of reverse transcriptase and protease inhibitors. More effective clinical management of patients is achieved if the drug-resistance mutations are identified early so that treatments can be adjusted to those that are effective against the particular strain (e.g., mutant) of HIV. In view of this, viral genotyping is becoming an established procedure for monitoring of patients on HAART and has a significant impact on patient survival.

Viruses bearing drug-resistance mutations cannot generally be identified unless they comprise a significant percentage of a patient's viral population. As a consequence, the drug-resistant viruses are usually identified relatively late in the process leading to drug failure. Therefore, there is an urgent need for approaches that provide early identification of drug-resistance viral variants in patients.

SUMMARY OF THE INVENTION

The invention is based on the discovery that even in patients having no virus detectable in the blood by known means, e.g., patients undergoing drug therapy, such as combination drug therapy, it is possible to assay for the presence of a drug resistant HIV by detecting 2-LTR (long terminal repeats) circles, e.g., in peripheral blood mononuclear cells (PMBCs), and examining the circles for the presence of mutations that confer drug resistance, e.g., known mutations. Thus, the invention features a new method of detecting polymorphisms that confer drug resistance in HIV infection and can be used to detect drug-resistant HIV before a subject develops symptoms typical of drug resistance. The invention features a method of detecting a drug-resistant HIV in a subject. The method includes the steps of obtaining a biological sample from a subject, isolating an HIV 2-LTR circle from the biological sample, and detecting a drug-resistance mutation in the HIV 2-LTR circle, such that the presence of a drug-resistance mutation in the HIV 2-LTR circle indicates the presence of a drug-resistant HIV in the subject. The method may further include the step of amplifying the 2-LTR circle (e.g., using the polymerase chain reaction). In some embodiments, the biological sample is from a subject (e.g., human or non-human primate) that is undergoing drug therapy that includes administering to the subject at least one HIV reverse transcriptase inhibitor, at least one HIV protease inhibitor, or at least one HIV reverse transcriptase inhibitor and at least one HIV protease inhibitor. The subject can be an HIV-1-positive mammal, e.g., anon-human primate or a human. In certain embodiments, the biological sample is a peripheral blood mononuclear cell. In some cases HIV viral RNA is not detected in the blood of the subject.

The invention also includes a method for determining a drug regime for treating a subject infected with HIV that includes the steps of obtaining a biological sample (e.g., a blood sample or peripheral blood monocytes) from the subject, isolating an HIV 2-LTR circle from the biological sample, determining whether a gene in the HIV 2-LTR circle has a drug-resistance mutation, and if a drug-resistance mutation is present in the gene, determining a drug regime for the subject such that the drug regime includes at least one drug against which the gene having a drug-resistance mutation does not confer drug resistance. The method may further include the step of amplifying the 2-LTR circle (e.g., using the polymerase chain reaction). In some embodiments, the biological sample is from a subject (e.g., a human or non-human primate) that is undergoing drug therapy that includes administering to the subject at least one HIV reverse transcriptase inhibitor, at least one HIV protease inhibitor, or at least one HIV reverse transcriptase inhibitor and at least one HIV protease inhibitor. The subject can be an HIV-1-positive mammal, e.g., a non-human primate or a human. In certain embodiments, the biological sample is a peripheral blood mononuclear cell. In some cases HIV viral RNA is not detected in the blood of the subject.

The invention can be used on a sample from any mammal that harbors or is suspected of harboring HIV including non-human primates (e.g., chimpanzees) and humans.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1B:
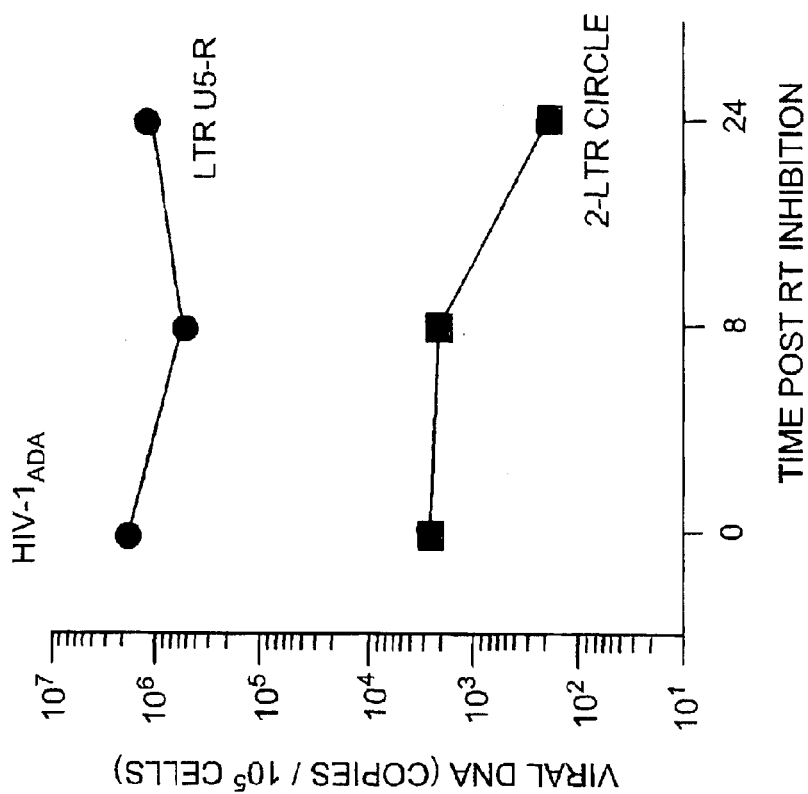
FIGS. 1A and 1B are graphs of viral DNA (copies/$10^5$ cells) versus time post RT inhibition, showing data for HIV-$1_{LA1}$ and HIV-$1_{ADA}$, respectively.

The invention relates to methods of detecting drug-resistant HIV variants in HIV-infected individuals by exploiting the discovery that HIV 2-LTR circles harboring mutations that confer drug resistance can be detected with great sensitivity. Thus, the invention is especially useful for early detection of drug-resistant HIV variants. The invention can also be used to design treatment regimes that are most likely to be effective for an individual, i.e., by designing treatment regimes that include one or more agents that are effective against HIV variants detected in the patient.

In vitro studies of retroviruses have shown that the first evidence of reverse transcription is unintegrated viral DNA appearing in the cytoplasm, which is transported to the nucleus within hours after infection of a cell (Shank et al., J. Virol. 25:104–114, 1978; Clayman et al., Science, 206:582–584, 1979; and Stevenson et al., EMBO J., 9:1551–1560, 1990). In the case of HIV-1, this unintegrated DNA exists in several forms, including incompletely or completely reverse-transcribed linear DNA, circular DNA containing one LTR, and circular DNA containing two LTRs (2-LTR circles). 2-LTR circles are identical to integrated proviruses, except that the ends of the LTR are joined in a head-to-tail fashion via a covalent linkage.

PCR can be used to specifically amplify a small segment (a few hundred base pairs) spanning the 2-LTR junction. The PCR is specific for 2-LTR circles, since no proviruses, single LTR circles, or other incomplete viral reverse transcription products will be amplified. Methods of detecting 2-LTR circles are described herein and in U.S. patent application Ser. No. 09/478,170, filed Jan. 5, 2000, and U.S. patent application Ser. No. 10/044,197, filed Jan. 10, 2002.

In HIV-infected individuals, the viral genome exists in many forms and a majority of the viral genomes are defective, i.e., they contain mutations in essential genes or they are in transcriptionally silent (latent) form. Many of these genomes do not contribute to viral replication. Detection of viral genomes harboring drug-resistant mutations can be obscured by these genomes, which are not drug-resistant. Using standard methods, the drug-resistant viruses must represent in excess of five to ten percent of the viral population in the clinical sample to be efficiently identified by standard sequencing methods. The low frequency of drug-resistant mutations in a background of drug-naïve genotypes greatly limits the ability to predict drug failure. In the present invention, replicating viruses, e.g., those expressed as 2-LTR circles, are amplified. In an individual developing drug resistance, it is the drug-resistant viruses that are replicating. Early detection of drug resistance is thus made possible by using a method in which 2-LTR sequences from a patient's sample are enriched as described herein, followed by genotyping of the amplified sequences.

The 2-LTR circle is a labile intermediate in the viral life cycle. The unique structure of the 2-LTR circle allows it to be selectively identified and discriminated from the background of non-replicating defective and latent viral genomes. Since the 2-LTR circle represents genomes formed as a result of ongoing and recent infection events, drug-resistance mutations are over-represented in these circles. Using the invention, the replicating circles are identified and examined for known and/or newly discovered drug resistance mutations in patients receiving drug therapy. The method uses amplification and sequencing of 2-LTR circle genomes from patients on HAART, and permits early identification of drug-resistance mutations in an infected subject. Furthermore, the 2-LTR circle represents a unique surrogate marker for demonstrating on-going replication in patients who have undetectable levels of viral RNA (e.g., while they are receiving HAART). This property is exploited to use circles to detect ongoing infection by drug-resistant virus in HIV-infected patients at very early stages of infection. Early identification of drug-resistant virus allows the clinician to make earlier adjustments to antiretroviral regimens to avoid drug failure.

The identification of drug-resistant variants in HIV-infected individuals involves initial amplification of the genes encoding the reverse transcriptase and protease genes by polymerase chain reaction. Drug resistance mutations in HIV have been identified (e.g., see D'Aquila et al., 2002, Topics in HIV Medicine, 10:11–15) and methods of identifying such drug-resistant mutations are known in the art. For example, identified mutations can be used to determine a "virtual" phenotype, i.e., the mutations identified in a patient sample are used to predict drug-sensitivities based on previously characterized drug-resistance mutations (Tibotex-Virco USA, Durham, N.C.). In another method, the reverse transcriptase and protease genes from a patient sample are inserted into an indicator virus and the viral sensitivity to various drug combinations is determined using in vitro drug culture assay systems (Virologic, South San Francisco, Calif.).

Sample Preparation

A variety of biological samples can be analyzed by the methods of the invention, including blood and solid-tissue biopsies (e.g., a lymph node biopsy). For example, blood can be collected from an HIV-positive individual undergoing combination therapy. Peripheral blood mononuclear cells (PBMC) are isolated by standard FICOLL™-based isolation procedures. The PBMC are then lysed and the total or extrachromosomal DNA isolated.

Total cellular DNA can be extracted by lysing the PBMC in detergent, digesting the cellular protein, and precipitating the DNA (Pauza et al., Virology, 205:470–478, 1984; and Panther et al., J. Acquir. Immune. Defic. Syndr. Hum. Retro. 17:303–313, 1998). Extrachromosomal DNA can be isolated by methods known in the art, including standard alkaline lysis, Hirt extraction, or guanidinium thiocyanate precipitation (Jurrians et al., J. Gen. Virol. 73:1537–1541, 1992; Stevenson et al., J. Virol. 64:2421–2425, 1990; and Sambrook et al., eds., *Molecular Cloning: A Laboratory Manual*. 2nd, ed., Cold Spring Harbor Laboratory, Cold Spring Harbor Laboratory Press, Cold Spring Harbor, N.Y., 1989).

Standard alkaline lysis technique, used for isolating plasmid DNA from bacteria, can also be used according to the invention to isolate 2-LTR circles from mammalian cells. The Spin Miniprep Kit available from Qiagen (Cat. No. 27104) is, for example, useful for this purpose. The methods of the invention include the use of this technique to isolate and purify 2-LTR circle DNA.

When possible, extrachromosomal DNA, instead of total DNA, should be isolated since the number of target 2-LTR circles per microgram of extrachromosomal DNA is expected to be greater than the number of 2-LTR circles per microgram of total cellular DNA.

Detecting 2-LTR Circles

2-LTR circles can be detected using known techniques, including those that do not require nucleic acid amplification, such as Southern blotting. The DNA sample obtained as described herein can be hybridized with 2-LTR circle-specific probes that are directly or indirectly labeled with chromogenic, radioactive, fluorescent, or luminescent labels.

Where amplification of the 2-LTR circles is desired, e.g., before a detection step, the 2-LTR circles can be amplified by any method well known in the art. These methods include polymerase chain reaction (PCR; U.S. Pat. Nos. 4,683,195 and 4,683,202) and variants thereof. Another suitable nucleic acid amplification method is ligation chain reaction (LCR) or variants thereof (Landegran et al., Science, 241:1077–1080, 1988; and Nakazawa et al., Proc. Natl. Acad. Sci. USA, 91:360–364, 1994).

Other amplification methods include: self-sustained sequence replication (Guatelli et al., Proc. Natl. Acad. Sci. USA, 87:1874–1878, 1990), transcriptional amplification system (Kwoh, et al., Proc. Natl. Acad. Sci. USA, 86:1173–1177, 1989), and Q-Beta Replicase (Lizardi et al., Bio/Technology, 6:1197, 1988).

However the 2-LTR circles are detected, a threshold level of 2-LTR circles per million cells is useful to define meaningful numbers of the circles. If the assay is capable of single-molecule sensitivity, a base threshold can be established at one circle per million PBMC. This threshold is appropriate when determining whether eradication of HIV has been achieved in a patient. Whenever a patient tests above this threshold, the patient is said to exhibit active viral infection. Whenever a patient tests below the threshold, the patient is said to have undetectable levels of infection and may be a candidate for removal from antiviral therapy. In other contexts, such as when the level of 2-LTR circles is used to determine the efficacy of any antiviral regime, thresholds above one per million PBMC can be appropriate (e.g., 10, 50, 100, or 250 circles/$10^6$ PBMC).

Any of the above methods can be combined in a method of the invention to achieve suitable 2-LTR detection efficiencies.

Methods for Detecting Polymorphisms in 2-LTR Circles

Polymorphisms in 2-LTR circles can be detected using methods known in the art. An example of such a method is detection of single nucleotide polymorphisms (SNP). Such polymorphisms can be detected using, e.g., molecular beacons (See Afonina et al., 2002, PharmaGenomics, January/February 48–54; Mhlanga et al., 2001, Methods 25:463–471; and Piatek et al., 1998, Nature Biotechnol. 16:359–363). Detection of polymorphisms associated with drug-resistance in HIV is useful for diagnosing and predicting drug resistance. In some embodiments of the invention, an assay is performed in which 2-LTR circles are amplified as described herein and polymorphisms in the amplified products are assessed, e.g., for polymorphisms known to be associated with a drug resistant HIV.

Administration of Antiviral Drugs

Dosages, specific formulations, and routes of administration of HIV antiviral drugs are known in the art. See, e.g., Physicians' Desk Reference, Fifty-fourth edition (Medical Economics Company, Montvale, N.J., 2000) and Kuritzkes et al. (1999, AIDS 13:685–694).

EXAMPLES

The invention will be further described in the following examples, which do not limit the scope of the invention described in the claims.

Example 1

Blood samples were obtained using standard techniques from 20 HIV-1-infected individuals who began and continued to receive combination anti-HIV drug therapy. All of these patients exhibited a period of time in which, after commencement of combination therapy, no plasma viral RNA could be detected by quantitative PCR. PBMC were isolated from each blood sample, and their extrachromosomal DNA was purified using the Spin Miniprep Kit available from Qiagen as Cat. No. 27104, generally following the manufacturer's directions.

HIV-12-LTR circles were detected by quantitative PCR using the 2-LTR-specific primers described in Stevenson et al., J. Virol. 64:2421–2425 (1990). The (−) strand primer spanned nucleotides 9591 to 9610 (or 507–526) of the HXB2 strain of HIV-1, while the (+) strand primer spanned nucleotides 9650–9669 (or 566–585) of the HXB2 strain of HIV-1 (Ratner et al., Nature, 313:277–284, 1985). Plasma viral RNA in each sample was also measured using the AMPLICOR® HIV Monitor Test kit (Roche Molecular Systems, Inc., Branchburg, N.J.), employing HIV-1-specific quantitative PCR, following manufacturer's directions. The threshold of detection for this standard HIV-1 RNA detection assay was about 50 viral RNA molecules per milliliter of plasma. On the other hand, the threshold for the method of the invention at which the number of 2-LTR circles was conservatively estimated to give a positive result was set at 1 molecule or circle per million PBMC (roughly about 0.1 to 1 ml whole blood). Higher thresholds could be set, but such thresholds may lead to more false negatives. Considering the consequences of false negatives, the lowest practical threshold should be used. The results are summarized in Table 1.

TABLE 1

| Patient | # Viral RNA/ml Plasma | # 2-LTR Circles/$10^6$ cells | Months without Detectable Viral RNA |
|---|---|---|---|
| 1 | <50 | 20 | N/A |
| 2 | 155 | 25 | 8 |
| 3 | <50 | 47 | 12 |
| 4 | <50 | 872 | 9 |
| 5 | N/A | 13 | N/A |
| 6 | <50 | <1 | 9 |
| 7 | <50 | 6200 | 7 |
| 8 | <50 | <1 | 17 |
| 9 | N/A | 1 | N/A |
| 10 | <50 | 1 | N/A |
| 11 | <50 | 240 | 19 |
| 12 | 121 | 36 | 19 |
| 13 | N/A | 3 | 15 |
| 14 | <50 | 48 | 10 |
| 15 | <50 | <1 | 24 |
| 16 | <50 | 1 | 9 |
| 17 | <50 | 3 | 15 |
| 18 | <50 | <1 | 16 |
| 19 | <50 | 271 | 15 |
| 20 | 69 | 117 | 4 |

Table 1 illustrates the unexpectedly superior sensitivity of 2-LTR circle detection as compared to the standard plasma viral load assay. Some HIV-positive individuals, who do not have detectable plasma virus, nevertheless harbor newly HIV-infected blood cells, as indicated by the presence of 2-LTR circles (i.e., patients 1–5, 7, 9–14, 16, 17, 19, and 20).

These individuals should not cease antiviral therapy, since infectious virus is still present in the body.

On the other hand, in some patients with undetectable plasma virus, no 2-LTR circles were detected in their PBMC (i.e., patients 6, 8, 15, and 18). These individuals may have completely eradicated HIV from their bodies, and are candidates for removal from antiviral therapy.

Example 2

The stability of 2-LTR circle forms of viral DNA were initially examined in acutely infected cells in vitro. $CD4^+$ MT-4 T cells and Jurkat-CCR5 cells were infected with the X4 variant HIV-$1_{LA1}$ and the R5 variant HIV-$1_{ADA}$, respectively. Synthesis of viral cDNA was allowed to proceed for 24 hours, and further rounds of virus infection and cDNA synthesis were then restricted by the addition of reverse transcriptase inhibitors ZDV (5 μM) or Nevirapine (1 μM) to HIV-$1_{LA1}$ and HIV-$1_{ADA}$ infected cells, respectively. Cells were then maintained in the presence of the RT inhibitors.

The experimental procedures used in Examples 2–4 are briefly described below.

Figure 3:
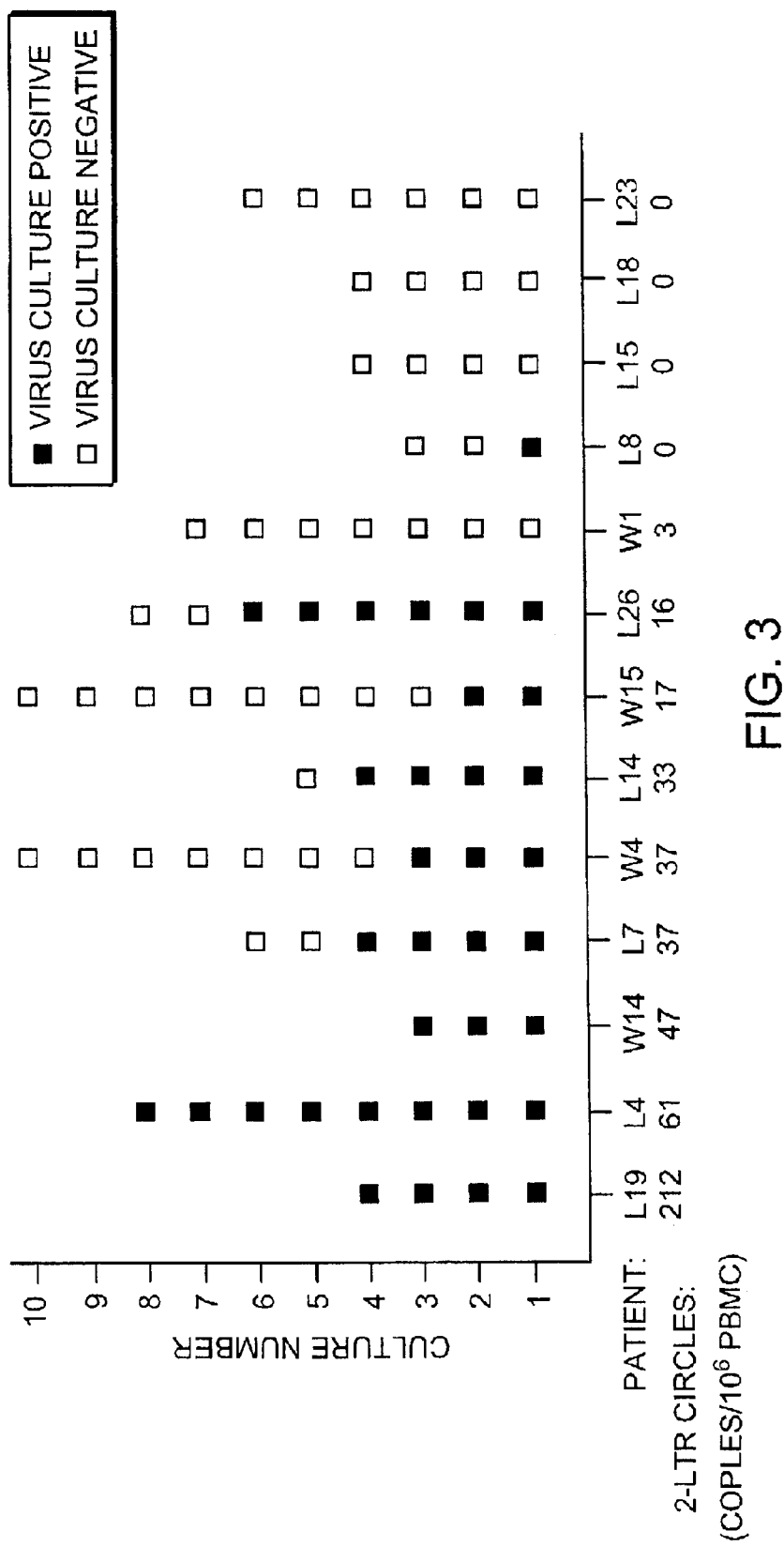
FIG. 3 is a data point plot of number of virus-positive and virus-negative cultures for patient designations.

The relationship between 2-LTR circle frequency and either the duration of undetectable plasma viral RNA or the frequency of positive virus co-cultures was examined using Spearman's correlation coefficient. Mean frequency of positive co-cultures in 2-LTR circle positive individuals and 2-LTR circle negative individuals as shown in FIG. 3 was further compared by a paired t-test.

FICOLL™-purified PBMC (2–40×10⁶) were collected by centrifugation at 1300×g for 2 minutes. Cell pellets were resuspended in buffer PI and extrachromosomal DNA was purified by a QIAprep™ spin miniprep kit (Qiagen, Valencia, Calif.) using the modification for the isolation of low copy number plasmids as recommended by the manufacturer. Chromosomal DNA was recovered from the sodium acetate—SDS precipitate using DNAzol™ reagent (Life Technologies, Gaithersburg, Md.) according to the manufacturer's protocol. Total cellular DNA was purified using an ISOQUICK™ nucleic acid extraction kit (ORCA Research, Bothell, Wash.).

2-LTR circle junctions were amplified from 10–30 μl of extrachromosomal DNA in a 50 μl reaction containing 1×HotStarTaq™ buffer, 200 nM dNTPs, 400 nM primers, and 1.5 units HotStarTaq™ (Qiagen, Valencia, Calif.). The reverse primer was 5'-cagatctggtctaaccagaga-3' (SEQ ID NO:1), and the forward primer was 5'-gtaactagagatccctcagac-3' (SEQ ID NO:2), which annealed to nucleotides 9157–9137 (HIV-1 LTR R region) and nucleotides 130–150 (HIV-1 LTR U5 region) of HIV-$1_{LAI}$, respectively (see GenBank Accession No. K02013 for numbering). After an initial denaturation step (95° C., 10 minutes), PCR amplification proceeded for 45 cycles (95° C., 30 seconds; 60° C., 30 seconds; 72° C., 60 seconds) followed by a final extension (72° C., 5 minutes).

To control for the effect of sequence polymorphisms at primer binding sites, amplification was performed with internal primers reversed in orientation compared to those listed above. Amplification with the internal LTR primers proceeded for 35 cycles using conditions outlined above. Polymorphisms in the region of the LTR that is recognized by the fluorogenic probe can affect annealing of the probe and potentially result in "false negatives." Consequently, Taqman reaction products were subsequently analyzed on agarose-TBE gels and stained with ethidium bromide to ensure that those reactions did not contain episome-specific PCR products. For quantitation of 2-LTR circle frequency in patient PBMCs, PCR reactions were performed using an ABI Prism® 7700 sequence detection system with the addition of 200 nM fluorogenic probe (5'-agtggcgagccctcagatgctgc-3'; SEQ ID NO:3) to the reaction. The probe anneals to nucleotides 9081–9103 of HIV-$1_{LA1}$ and was modified with 6-FAM (6-carboxyfluorescein) reporter dye on the 5' end and 6-TAMRA (6-carboxytetramethylrhodamine) quencher dye on the 3' end. Copy number estimates of 2-LTR circles were determined by extrapolation from a plot of standards versus band intensity or by using the ABI prism 7700 quantitation software. For sequencing, 2-LTR circle junctions were cloned into a TA cloning vector (Invitrogen, San Diego, Calif.) and analyzed on an ABI 377 DNA sequencer according to the manufacturer's protocol.

Patient PBMC were separated by Ficoll-Paque™ (Amersham-Pharmacia) and depleted of $CD8^+$ T lymphocytes using antibody-coated beads (Dynal). Cells were seeded in flasks in aliquots of $1 \times 10^7$ cells in RPMI 1640 medium supplemented with 10% fetal calf serum and activated by phytohaemaglutinin (PHA; 5 μg/ml) for 12 hours. $CD8^+$-depleted PBMC from HIV-1 seronegative individuals were activated for 12 hours with PHA and added in equal numbers to flasks of patient PBMC together with 20 IU/ml of interleukin-2 (IL-2; Genzyme). At weekly intervals, half of the culture supernatant was replaced with fresh medium containing 20 IU/ml IL-2 and $10^7$ freshly isolated, $CD8^+$-depleted, PHA-activated donor PBMC from HIV-1 seronegative individuals. HIV-1 Gag p24 antigen in culture supernatants was evaluated by ELISA (Beckman Coulter) after 4 weeks.

Figure 1A:
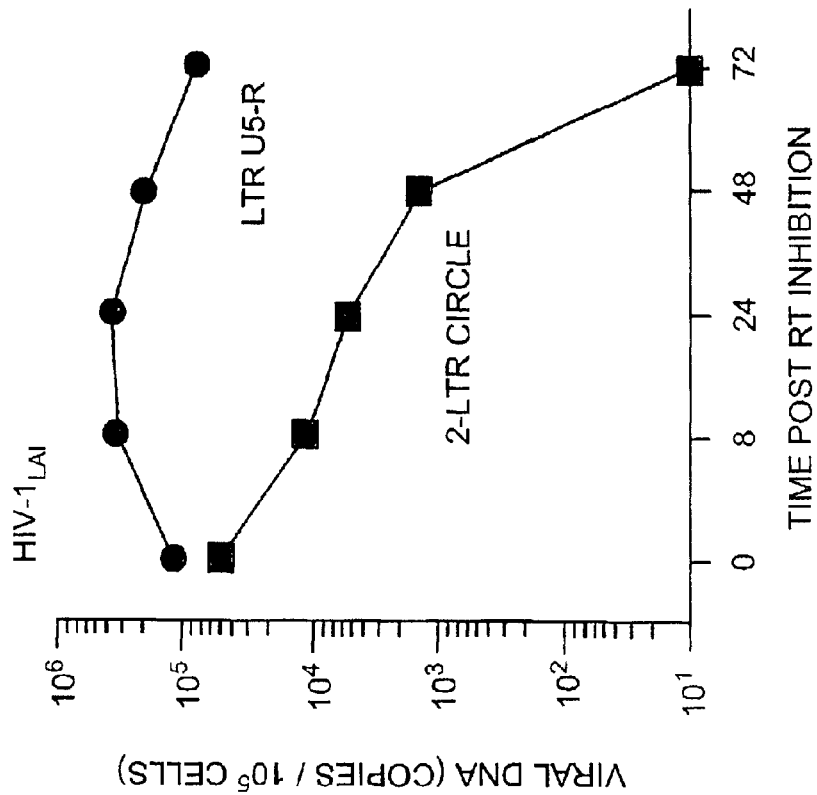

Within 24–48 hours following addition of the RT inhibitors, 2-LTR circle number fell by over ten fold in both HIV-$1_{LA1}$ and HIV-$1_{ADA}$ infected cells (FIGS. 1A and 1B). The copy number of other viral DNA forms identified by the internal LTR primers (predominantly linear and integrated viral genomes) remained relatively constant over the same interval. Thus, 2-LTR circles are labile intermediates in the virus lifecycle.

Example 3

Figure 2B:
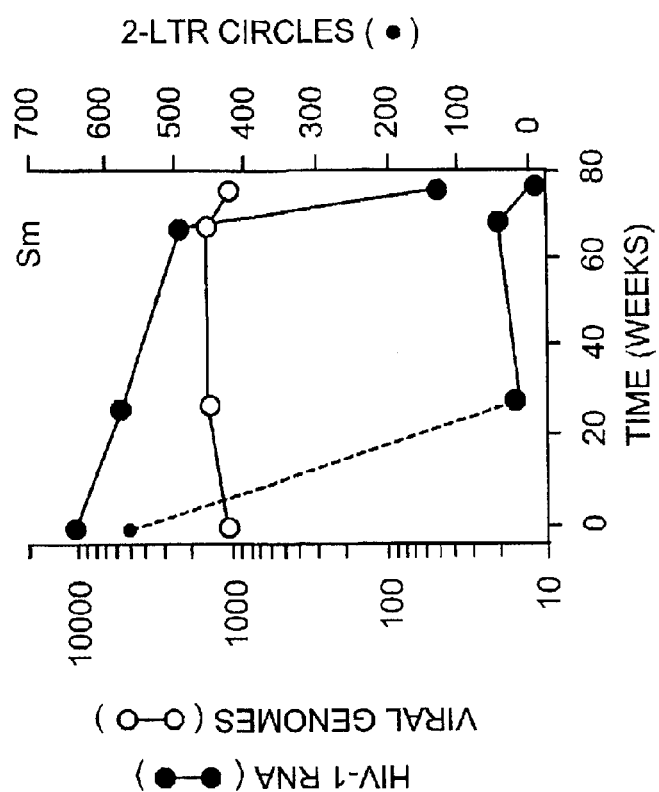
FIGS. 2A–2D are graphs of HIV-1 RNA or genomes versus time in weeks, showing the data for patients Gu, Sm, Za, and Ha, respectively.
Figure 2A:
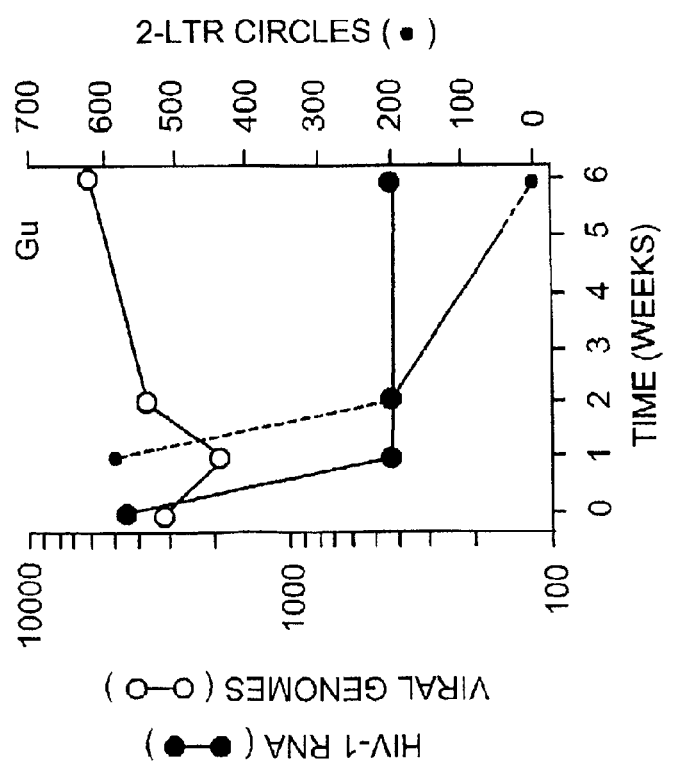
Figure 2D:
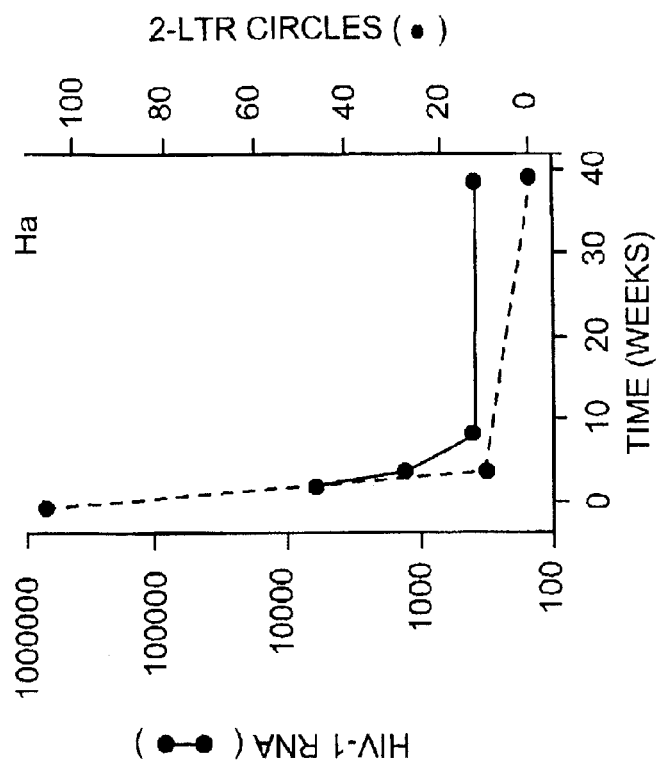
Figure 2C:
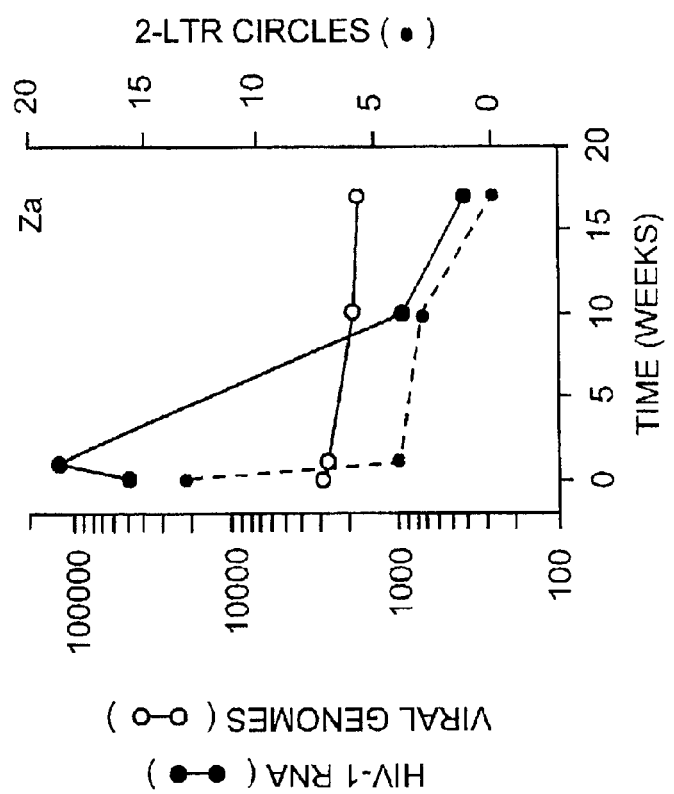

The lability of 2-LTR circles in vivo was evaluated. PBMC samples were obtained from four HIV-1 infected individuals (Gu, Sm, Za, Ha) who, following adjustment of their antiretroviral regimens to more potent combinations, exhibited steady declines in plasma viral RNA levels. Patient Gu, who had been maintained on a two-drug RT inhibitor combination, was subsequently changed (week 0) to a three-drug regimen (ZDV/3TC®/NFV). Patient Sm, who had been on a two-drug regimen (ZDV/3TC®) was changed at week 68 to ddI/EFV/NFV. Patient Za, who had been on a four-drug regimen (3TC®/D4T/ddI/NFV) was adjusted (week 1) to ZDV/ddC/NFV/RTV. Patient Ha, previously on a three-drug regimen (ZDV/ddI/NVP) was subsequently adjusted (week 0) to D4T/$3TC$®/NVP. Marked declines in 2-LTR circle copy number were observed over the interval in which there was a rapid drop in levels of plasma viral RNA (FIGS. 2A–2D). In contrast, when samples were analyzed in parallel with internal LTR primers, HIV-1 viral genome levels (detected via cDNA) fluctuated by no more than three fold (FIGS. 2A–2C). Collectively, the results demonstrate that 2-LTR circles are labile, both in vitro and in vivo, relative to integrated viral genomes. The result is important to the new assay methods because if the LTR circles were stable they could not serve as reliable indicators of newly infected cells.

Example 4

A larger patient population than that of Example 1 was then examined. The 2-LTR HIV-1 episomes of 63 patients (four of whom were included in the study described in Example 1) were examined who, through treatment with high activity antiretroviral therapy (HAART), had undetectable levels of plasma viral RNA for sustained periods of time (Table 2). Fifty of these patients (80%) had undetectable levels of plasma viral RNA (assay limit of sensitivity was 400 copies/ml) for 12 months or longer (Table 2). Of these 50 patients, 24 (48%) exhibited undetectable levels of plasma viral RNA for 12 months or more using an assay with a sensitivity of 50 copies/ml. In 48 of the 63 patients (76%), 2-LTR circles were detected in their PBMC (Table 2). 2-LTR circle copy numbers ranged from less than 1 copy/$10^6$ PBMC to 620 copies/$10^6$ PBMC. There did not appear to be any significant relationship between the frequency of 2-LTR circles in patient PBMCs and the time during which plasma viral RNA was undetectable. These data indicate that labile replication intermediates are present in a substantial proportion of HIV-1 infected individuals who exhibit sustained suppression of plasma viral RNA while on HAART. 2-LTR circles were not detectable in PBMC from 15 (24%) patients (Table 2).

Table 2 (below) lists AIDS patients on HAART and the level of 2-LTR circles and viral RNA in the blood. The abbreviations for Table 2 are as follows. Anti-retroviral therapy: ZDV, Zidovudine; 3TC® (lamivudine); D4T, stavudine; ddl, didanosine; NVP, nevirapine; RTV, ritonavir; EFV, efavirenz; SQV, saquinavir; IDV, indinavir; NFV, nelfinavir; ddC, zalcitabine; and ABV, abacavir. CD4+ T cell measurements were determined at or just prior to time PBMC were collected for PCR analysis of viral cDNA intermediates.

For the column in Table 2 labeled "Period of Undetectable Viral RNA," plasma viral RNA was detected using an assay with a sensitivity of about 400 copies/ml. Numbers in parentheses indicate the period for which viral RNA was below the level of detection using a second assay with a sensitivity of 50 copies/ml. Plasma viral RNA measurements were determined approximately every three months.

The 2-LTR circle copy number in most cases was determined in duplicate on independent PBMC samples. Values less than 1 indicated that more than 1 million PBMC were required for detection of 2-LTR circles.

The total number of PBMC from which extrachromosomal DNA was isolated and analyzed for the presence of 2-LTR circles was determined as follows. In all patients, 2-LTR circles were quantitated by fluorescence-based PCR using Taqman software (ABI Prism 7700 Software). Similar 2-LTR circle numbers were obtained when samples were quantitated by comparison of PCR band intensity to a standard dilution of synthetic 2-LTR circles.

TABLE 2

| Patient Number | Drug Regiments | CD4+ T Cells (cells/ml) | Period of Undetectable Viral RNA (months) | 2-LTR circles (Copies/$10^6$ PBMC) | # PBMC Analyzed (millions) |
|---|---|---|---|---|---|
| W1 | RTV, ZDV, 3TC | 475 | 23 (14) | 3 | 1.0 |
| W2 | NFV, ZDV, 3TC | 827 | 13 (13) | <1 | 5.5 |
| W3 | IDV, D4T, 3TC | 436 | 23 (14) | 27 | 1.0 |
| W4 | IDV, D4T, 3TC | 505 | 22 (12) | 37 | 1.0 |
| W6 | IDV, D4T, 3TC | 248 | 19 (11) | 15 | 1.0 |
| W7 | SQV, D4T, 3TC | 443 | 19 (13) | 8 | 1.0 |
| W8 | ddl, D4T | 870 | 18 (15) | <1 | 4.0 |
| W9 | NFV, D4T, 3TC | 641 | 22 (11) | 59 | 1.0 |
| W10 | IDV, ZDV, 3TC | 656 | 22 (15) | <1 | 4.0 |
| W11 | IDV, ZDV, 3TC | 344 | 22 (15) | 65 | 1.0 |
| W12 | ZDV, 3TC, DLV | 626 | 26 (16) | <1 | 5.5 |
| W13 | NFV, ZDV, 3TC | 699 | 13 (13) | <1 | 5.5 |
| W14 | NFV, D4T, 3TC | 685 | 21 (15) | 47 | 1.0 |
| W15 | NFV, STC, NVP | 866 | 25 (12) | 17 | 1.0 |
| W16 | RTV, D4T, 3TC | 572 | 22 (14) | 2 | 5.5 |
| W17 | IDV, ZDV, 3TC | 364 | 26 (15) | 31 | 1.0 |
| W18 | IDV, ZDV, 3TC | 119 | 21 (16) | <1 | 2.0 |
| W19 | SQV, ZDV, 3TC | 153 | 16 (10) | 4 | 4.0 |
| W20 | IDV, ZDV, 3TC | 360 | 27 (15) | <1 | 4.0 |
| W21 | NFV, D4T, 3TC | 208 | 13 (13) | <1 | 2.0 |
| W22 | D4T, 3TC | 495 | 23 (15) | <1 | 4.0 |
| W28 | NFV, ddl, D4T | 527 | 22 (8) | 9 | 1.0 |
| W30 | D4T, 3TC | 575 | 22 (17) | <1 | 4.0 |
| M1 | NFV, D4T, NVP | 287 | 14 (9) | 31 | 1.0 |
| M3 | IDV, ddl, NVP | 440 | 16 (7) | 22 | 1.0 |
| M4 | IDV, ZDV, 3TC | 586 | 13 (ND) | 264 | 1.0 |
| M6 | NFV, ZDV, 3TC | 317 | 24 (7) | 63 | 1.0 |
| M7 | NFV, 3TC, NVP | 175 | 11 (ND) | 4 | 5.5 |
| M8 | IDV, ZDV, 3TC, NVP | 357 | 13 (2) | 15 | 1.0 |
| M12 | NFV, D4T, 3TC | 749 | 12 (7) | 35 | 1.0 |
| M13 | ZDV, 3TC, EFV | 670 | 10 (0) | 67 | 1.0 |
| M14 | IDV, ZDV, 3TC | 728 | 14 (14) | 41 | 1.0 |
| M15 | IDV, ZDV, 3TC | 565 | 10 (10) | 82 | 1.0 |
| M16 | NFV, 3TC, NVP | 403 | 12 (8) | 3 | 4.0 |
| L2 | 3TC, D4T, RTV | 852 | 8 (8) | 5 | 1.0 |
| L3 | ZDV, 3TC, IDV | 448 | 12 (8) | 10 | 1.0 |
| L4 | ZDV, 3TC, RTV | 978 | 21 (12) | 180 | 1.0 |
| L6 | D4T, RTV, SQV | 577 | 10 (7) | <1 | 4.0 |
| L7 | D4T, ddl, NVP | 394 | 11 (7) | 610 | 1.0 |
| L8 | ZDV, 3TC, NFV | 173 | 17 (8) | <1 | 1.0 |
| L9 | 3TC, D4T, EFV | 482 | 8 (5) | <1 | 2.2 |

TABLE 2-continued

| Patient Number | Drug Regiments | CD4+ T Cells (cells/ml) | Period of Undetectable Viral RNA (months) | 2-LTR circles (Copies/10^6 PBMC) | # PBMC Analyzed (millions) |
|---|---|---|---|---|---|
| L11 | ZDV, 3TC, RTV | 615 | 19 (12) | 84 | 1.0 |
| L12 | 3TC, D4T, RTV | 389 | 19 (6) | 7 | 1.0 |
| L13 | D4T, SQV, NFV | 312 | 15 (3) | <1 | 7.8 |
| L14 | 3TC, D4T, IDV | 375 | 14 (7) | 116 | 1.0 |
| L15 | 3TC, RTV, SQV, ABV | 91 | 30 (17) | <1 | 1.5 |
| L16 | 3TC, D4T, SQV, RTV | 575 | 12 (12) | 4 | 8.1 |
| L17 | 3TC, D4T, SQV | 198 | 15 (15) | 14 | 1.0 |
| L18 | ZDV, 3TC, IDV | 175 | 16 (13) | <1 | 10.2 |
| L19 | 3TC, D4T, RTV, SQV | 499 | 15 (6) | 620 | 1.0 |
| L22 | ZDV, D4T, IDV | 223 | 14 (12) | 6 | 1.0 |
| L23 | 3TC, ddC, IDV | 534 | 14 (12) | <1 | 4.8 |
| L26 | 3TC, D4T, SQV, NFV | 911 | 17 (6) | 36 | 1.0 |
| L27 | ZDV, 3TC, IDV | 185 | 17 (17) | <1 | 3.2 |
| L28 | D4T, ABV, EFV | 80 | 8 (8) | 275 | 1.0 |
| L29 | ZDV, ddC, SQV, NFV | 121 | 21 (1) | 3 | 2.0 |
| L32 | 3TC, D4T, EFV | 219 | 7 (1) | <1 | 10.0 |
| L33 | 3TC, D4T, IDV | 610 | 16 (1) | <1 | 14.4 |
| L36 | ddI, D4T, NFV | 172 | 14 (4) | 2 | 5.6 |
| L37 | ZDV, ddC, 3TC, IDV | 279 | 13 (7) | <1 | 5.6 |
| L41 | ZDV, 3TC, RTV | 990 | 22 (1) | 100 | 1.0 |
| L42 | 3TC, D4T, SQV | 117 | 18 (1) | <1 | 2.0 |
| L46 | 3TC, D4T, NFV | 180 | 7 (1) | 4 | 20.0 |

It was suspected that in 2-LTR circle-positive patients, there would also be cells harboring replication competent virus. To investigate this, high-input viral co-culture assays were performed on PBMC from nine 2-LTR circle positive and four 2-LTR circle negative patients. The results are shown in FIG. 3. Replication competent virus was isolated from eight of the nine patients who were 2-LTR circle positive. Virus could not be isolated from patient WI who had a very low circle copy number. In addition, infectious virus could not be isolated from three patients who were 2-LTR circle negative even though co-culture was conducted on between 40 and 60 million CD8+-depleted patient PBMCs. In patient L8 who was also 2-LTR circle negative, only one of three cultures yielded infectious virus (FIG. 3). Collectively, these results show a correlation between the presence of 2-LTR circles and cells harboring replication competent virus. Plasma based viral RNA assays therefore, unlike the 2-LTR circle assay, failed to reveal the full extent of viral activity in infected individuals who are being treated with HAART.

This study has important implications for the strategies to eradicate, inhibit, or minimize virus replication in HIV-1 infected individuals. Although complete elimination of HIV-1 replication may be difficult with current antiretroviral regimens, this study suggests instances in which even the most sensitive assays fail to reveal on-going replication in some well suppressed patients. It is also likely that, as more potent antiretroviral drugs enter the clinic, ongoing or "covert" virus replication may be arrested in a higher percentage of patients. A better understanding of the nature of the reservoir that sustains virus replication in aviremic patients on HAART may lead to the development of more effective strategies for arrest of virus replication. Monitoring of the 2-LTR, as a superior surrogate marker for viral replication, can be integral to the understanding of viral reservoirs. This method is therefore useful in conducting trials to determine whether a new drug is useful for modulating or stopping viral replication.

Example 5

Detection of Antiretroviral Drug Resistance Using 2-LTR Analysis

Patients receiving anti-retroviral therapies generally develop drug resistance. It is useful to predict the onset of drug resistance as soon as possible so that the patient's treatment regime can be altered accordingly.

An analysis was undertaken of a subset of clinical samples obtained from the AIDS Clinical Trial Group 306 study. Long PCR products were synthesized using primers that are specific for amplification of 2-LTR circular HIV-1 genomes. DNA sequence analysis of the reverse transcriptase gene region revealed the presence of mutations commonly associated with resistance to the drug regimens used in this trial. In particular, these tests revealed the presence of M184V, R211K, and L214F mutations, known to contribute to the ability of HIV-1 to replicate in the presence of the reverse transcriptase inhibitors.

2-LTR circle-based genotyping was performed in a sample from a patient enrolled in ACTG trial 306 who was treated with a combination of AZT, 3TC®, and d4T. Plasma HIV RNA was monitored over a 48 week period (FIG. 4) and peripheral blood mononuclear cells (PMBCs) were collected from the patient and stored frozen.

Extrachromosomal DNA containing 2-LTR circular HIV-1 templates was purified from PBMCs using a modified plasmid isolation kit (Qiagen #21704). The polymerase gene region of HIV-1 was amplified by PCR using a nested approach. The first round of PCR was for 30 cycles using twenty-five percent of the purified extrachromosomal DNA and 2-LTR circle template-specific primers. Two percent of the primary PCR products were then amplified in 20 cycles using primers flanking the pol region. The PCR products were purified and directly sequenced to detect mutations known to confer resistance to antiretroviral compounds.

Figure 4:
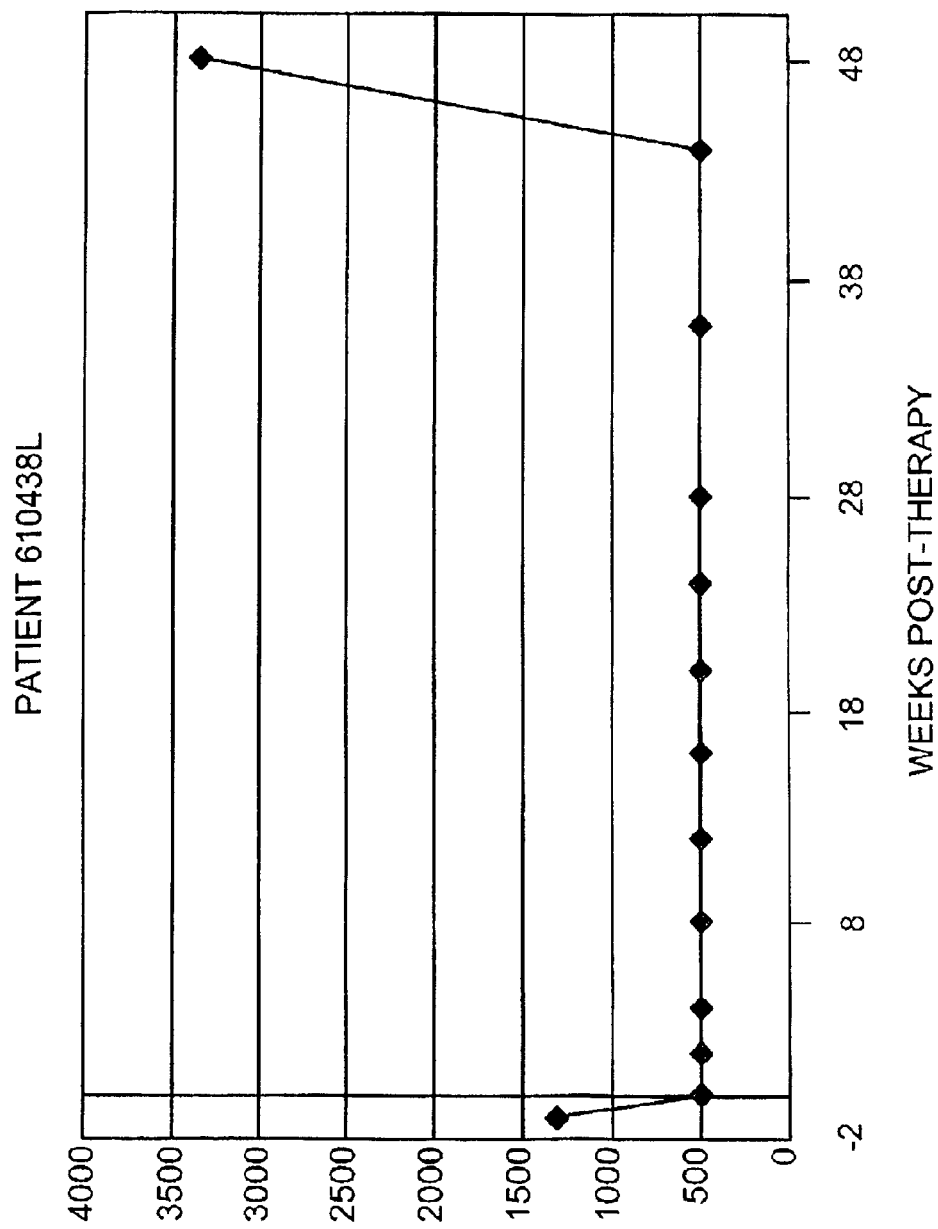
FIG. 4 is a graph showing the concentration (copies/ml) of HIV RNA in patient 610438L during combination (HAART) treatment.

Analysis of the 2-LTR samples showed that a resistance mutation was detectable in this patient at week 12 (Table 3) and breakthrough, as evidenced by viremia, occurred at week 48 (FIG. 4). In Table 3, the headings M184, R211, and L214 indicate the wildtype consensus amino acids (M, R, and L) at the respective loci (184, 211, and 214). The amino acids listed under each heading indicate the amino acid(s) identified at that locus at each time point. The R211 mutation is a relatively common polymorphism that is observed in HIV obtained from patients who are not on drug therapy. It may enhance the drug-resistance properties of the M184V mutation. These data demonstrate that drug resistance mutations can be identified in 2-LTR circles at least 36 weeks before a patient begins to fail therapy, e.g., at 12 weeks compared to 48 weeks.

TABLE 3

| Time (wks) | RNA (copies/ml) | M184 | R211 | L214 |
|---|---|---|---|---|
| −1 | 1318 | M | nd | F |
| 0 | 500 | nd | nd | F |
| 2 | 500 | M | R | F |
| 4 | 500 | M | K | F |
| 8 | 500 | M | K | F |
| 12 | 500 | V | K | F |
| 16 | 500 | M | R | F |
| 20 | 500 | M | K | F |
| 24 | 500 | M/V | K | F |
| 28 | 500 | V | K | F |
| 36 | 500 | V | K | F |
| 44 | 500 | V | K | F |
| 48 | 3367 | V | K | F | nd = not determined

Since bulk sequencing of PCR products can only reveal the majority sequence for a given sample, methods that detect multiple polymorphisms (e.g., using hybridization-based fluorescent oligonucleotide probes) can be used to more specifically identify polymorphisms in viral genomes (e.g., using molecular beacons). Such information can be useful for tailoring a patient's therapy to avoid treatments to which they will become resistant. The methods described herein can also be used to detect the presence of drug resistant HIV in newly-infected individuals.

Other Embodiments

It is to be understood that while the invention has been described in conjunction with the detailed description thereof, the foregoing description is intended to illustrate and not limit the scope of the invention, which is defined by the scope of the claims. Other aspects, advantages, and modifications are within the scope of the following claims.

What is claimed is:

1. A method of detecting a drug-resistant HIV in a subject, the method comprising
   a) obtaining a biological sample from a subject,
   b) selectively purifying extrachromosomal DNA from the sample, wherein the extrachromosomal DNA comprises an HIV 2-LTR circle,
   c) specifically amplifying a region of 2-LTR circular genome comprising a sequence, mutation of which confers drug resistance, and
   d) detecting a drug-resistance mutation in the amplified region of the HIV 2-LTR circle,
   wherein the presence of a drug-resistance mutation in the HIV 2-LTR circle indicates the presence of a drug-resistant HIV in the subject.

2. The method of claim 1, wherein the region of the 2-LTR circular genome is amplified using a polymerase chain reaction.

3. The method of claim 1, wherein the subject is undergoing drug therapy that comprises administering to the subject at least one HIV reverse transcriptase inhibitor.

4. The method of claim 3, wherein the drug therapy further comprises administering to the subject at least one HIV protease inhibitor.

5. The method of claim 1, wherein the subject is undergoing drug therapy that comprises administering to the subject at least one HIV protease inhibitor.

6. The method of claim 1, wherein the subject is an HIV-1-positive mammal.

7. The method of claim 1, wherein the subject is a non-human primate.

8. The method of claim 1, wherein the subject is a human.

9. The method of claim 1, wherein the biological sample is a peripheral blood mononuclear cell.

10. The method of claim 1, HIV viral RNA is not detected in the blood of the subject.

11. A method for determining a drug regime for treating a subject infected with HIV, the method comprising
    a) obtaining a biological sample from the subject,
    b) selectively purifying extrachromosomal DNA from the sample, wherein the extrachromosomal DNA corn rises an HIV 2-LTR circle,
    c) specifically amplifying a region of 2-LTR circular genome comprising a sequence, mutation of which confers drug resistance,
    d) determining whether a gene in the amplified region of the HIV 2-LTR circle has a drug-resistance mutation, and
    e) a drug-resistance mutation is present in the gene, determining a drug regime for the subject such that the drug regime comprises a drug against which the gene having a drug-resistance mutation does not confer drug resistance.

12. The method of claim 11, wherein the region of the 2-LTR circular genome is amplified using polymerase chain reaction.

13. The method of claim 11, wherein the subject is undergoing drug therapy that comprises administering to the subject at least one HIV reverse transcriptase inhibitor.

14. The method of claim 13, wherein the drug therapy further comprises administering to the subject at least one HIV protease inhibitor.

15. The method of claim 11, wherein the subject is undergoing drug therapy that comprises administering to the subject at least one HIV protease inhibitor.

16. The method of claim 11, wherein the subject is an HIV-1-positive mammal.

17. The method of claim 11, wherein the subject is a non-human primate.

18. The method of claim 11, wherein the subject is a human.

19. The method of claim 11, wherein the biological sample is a peripheral blood mononuclear cell.

20. The method of claim 11, wherein viral is not detected in the blood of the subject.

21. The method of claim 1, wherein specifically amplifying a region of 2-LTR circular genome comprises performing two rounds of amplification using a polymerase chain reaction-based method.

22. The method of claim 11, wherein specifically amplifying a region of 2-LTR circular genome comprises performing two rounds of amplification using a polymerase chain reaction-based method.

23. The method of claim 1, wherein the region of 2-LTR circular genome that is specifically amplified comprises a portion of a reverse transcriptase gene or a protease gene that is sufficient to detect the presence of a drug-resistance mutation in the gene.

24. The method of claim 11, wherein the region of 2-LTR circular genome that is specifically amplified comprises a portion of a reverse transcriptase gene or a protease gene that is sufficient to detect the presence of a drug-resistance mutation in the gene.

* * * * *

SEQUENCE LISTING

<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: synthetic primer

<400> SEQUENCE: 1
cagatctggt ctaaccagag a                                    21

<210> SEQ ID NO 2
<211> LENGTH: 21
<212> TYPE: DNA
<213> ORGANISM: Artificial Sequence
<220> FEATURE:
<223> OTHER INFORMATION: synthetic primer

<400> SEQUENCE: 2
gtaactagag atccctcaga c                                    21

<210> SEQ ID NO 3
<211> LENGTH: 23
<212> TYPE: DNA
<213> ORGANISM: Artificial Sequence
<220> FEATURE:
<223> OTHER INFORMATION: synthetic probe

<400> SEQUENCE: 3
agtggcgagc cctcagatgc tgc                                  23